United States Patent
Nair et al.

(10) Patent No.: US 7,074,188 B2
(45) Date of Patent: Jul. 11, 2006

(54) SYSTEM AND METHOD OF CHARACTERIZING VASCULAR TISSUE

(75) Inventors: Anuja Nair, Cleveland Heights, OH (US); D. Geoffrey Vince, Avon Lake, OH (US); Jon D. Klingensmith, Shaker Heights, OH (US); Barry D. Kuban, Avon Lake, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 130 days.

(21) Appl. No.: 10/647,971

(22) Filed: Aug. 25, 2003

(65) Prior Publication Data

US 2004/0122326 A1 Jun. 24, 2004

Related U.S. Application Data

(60) Provisional application No. 60/406,183, filed on Aug. 26, 2002, provisional application No. 60/406,254, filed on Aug. 26, 2002, provisional application No. 60/406,148, filed on Aug. 26, 2002, provisional application No. 60/406,184, filed on Aug. 26, 2002, provisional application No. 60/406,185, filed on Aug. 26, 2002, provisional application No. 60/406,234, filed on Aug. 26, 2002.

(51) Int. Cl.
*A61B 8/00* (2006.01)
*A61B 8/12* (2006.01)

(52) U.S. Cl. ............... 600/443; 600/463; 600/467
(58) Field of Classification Search ............ 600/443, 600/447, 455–456, 463, 467, 407, 471; 128/916; 382/128, 195, 287, 294
See application file for complete search history.

(56) References Cited

U.S. PATENT DOCUMENTS

| | | | |
|---|---|---|---|
| 4,228,804 A | 10/1980 | Holasek | |
| 4,511,984 A | 4/1985 | Sumino | |
| 4,561,019 A | 12/1985 | Lizzi | |
| 4,575,799 A | 3/1986 | Miwa | |
| 4,768,516 A | 9/1988 | Stoddart | |
| 4,803,994 A | 2/1989 | Burke | |
| 4,817,015 A | 3/1989 | Insana | |
| 4,858,124 A | 8/1989 | Lizzi | |
| 4,982,339 A | 1/1991 | Insana | |
| 5,097,836 A | 3/1992 | Yamada | |
| 5,235,984 A | 8/1993 | D'Sa | |
| 5,363,850 A | 11/1994 | Soni | |
| 5,417,215 A | 5/1995 | Evans | |
| 5,445,155 A | 8/1995 | Sieben | |
| 5,638,823 A | 6/1997 | Akay | |
| 5,724,972 A | 3/1998 | Petrofsky | |
| 5,746,209 A | 5/1998 | Yost | |
| 5,876,343 A | 3/1999 | Teo | |
| 5,885,218 A | 3/1999 | Teo | |
| 5,938,607 A | 8/1999 | Jago | |
| 5,957,138 A | 9/1999 | Lin | |
| 6,007,489 A | 12/1999 | Yost | |
| 6,050,946 A | 4/2000 | Teo | |
| 6,066,098 A | 5/2000 | Masotti | |
| 6,086,539 A | 7/2000 | Guracar | |
| 6,095,976 A | 8/2000 | Nachotomy | |
| 6,106,460 A | 8/2000 | Panescu | |
| 6,106,465 A | 8/2000 | Napolitano | |
| 6,120,445 A | 9/2000 | Grunwald | |
| 6,152,878 A | 11/2000 | Nachotomy | |
| 6,154,518 A * | 11/2000 | Gupta | 378/62 |
| 6,165,128 A * | 12/2000 | Cespedes et al. | 600/463 |
| 6,200,268 B1 * | 3/2001 | Vince et al. | 600/443 |
| 6,217,517 B1 | 4/2001 | Grunwald | |
| 6,238,342 B1 | 5/2001 | Feleppa | |
| 6,254,541 B1 | 7/2001 | Teo | |
| 6,264,609 B1 * | 7/2001 | Herrington et al. | 600/443 |
| 6,287,259 B1 | 9/2001 | Grunwald | |
| 6,306,089 B1 | 10/2001 | Coleman | |
| 6,335,980 B1 | 1/2002 | Armato | |
| 6,381,350 B1 | 4/2002 | Klingensmith et al. | |
| 6,415,046 B1 * | 7/2002 | Kerut, Sr. | 382/128 |
| 6,454,715 B1 | 9/2002 | Teo | |
| 6,464,640 B1 | 10/2002 | Guracar | |
| 6,514,202 B1 | 2/2003 | Grunwald | |

| | | | |
|---|---|---|---|
| 6,514,203 B1 | 2/2003 | Bukshpan | |
| 6,544,187 B1 | 4/2003 | Seward | |
| 6,561,980 B1 | 5/2003 | Gheng | |
| 6,597,943 B1* | 7/2003 | Taha et al. | 600/515 |
| 6,659,953 B1 | 12/2003 | Sumanaweera | |
| 6,776,760 B1* | 8/2004 | Marmarelis | 600/448 |
| 6,817,982 B1* | 11/2004 | Fritz et al. | 600/443 |
| 6,835,177 B1* | 12/2004 | Fritz et al. | 600/443 |
| 2001/0014774 A1 | 8/2001 | Grunwald | |
| 2003/0028118 A1 | 2/2003 | Dupree | |
| 2003/0092993 A1 | 5/2003 | Grunwald | |
| 2005/0124881 A1 | 6/2005 | Kanai | |

FOREIGN PATENT DOCUMENTS

| | | |
|---|---|---|
| JP | 2002-074957 | 3/2002 |
| WO | WO 94/23652 | 10/1994 |
| WO | WO 99/46731 | 9/1999 |

OTHER PUBLICATIONS

Nair, A., Kuban, B., Obuchowski, N., and Vince, D., "Assessing Spectral Algorithms to Predict Atherosclerotic Plaque Composition With Normalized and Raw Intravascular Ultrasound Data", Ultrasound in Medicine and Biology, 2001, pp. 1319-1331, vol. 27, No. 10, Elsevier, U.S.A.

Nair, A., Kuban, B., Tuzcu, E., Schoenhagen, P., Nissen, S., and Vince, D., "Coronary Plaque Classification With Intravascular Ultrasound Radiofrequency Data Analysis", Circulation, 2002, pp. 2200-2206; 106, American Heart Association, U.S.A.

Klingensmith, J. and Vince, D., "B-Spline Methods for Interactive Segmentation and Modeling of Lumen and Vessel Surfaces in Three-Dimensional Intravascular Ultrasound," Computerized Medical Imaging and Graphics 26, 2002, pp. 429-438, Elsevier Science Ltd., U.S.A.

Aydin, N., Padayachee, S., Markus, H., "The Use of the Wavelet Transform to Describe Embolic Signals", Ultrasound in Medicine and Biology, 1999, pp. 953-958, vol. 25, No. 6, Elsevier, New York, U.S.A.

Baldeweck, T., Laugier, P., Herment, A., Berger, G., "Application of Autoregressive Spectral Analysis for Ultrasound Attenuation Estimation: Interest in Highly Attenuating Medium", IEEE Transactions on Ultrasonics, Ferroelectrics, and Frequency Control, 1995, pp. 99-110, vol. 42, No. 1, Institute of Electrical and Electronics Engineers, New York, U.S.A.

Bookstein, F., "Principal Warps: Thin-Plate Splines and the Decomposition of Deformations", IEEE Transactions on Pattern Analysis and Machine Intelligence, 1989, pp. 567-585, vol. 11, No. 6, IEEE Computer Society, New York, U.S.A.

Bookstein, F., *Morphometric Tools for Landmark Data: Geometry and Biology*, 1991, pp. 55-87, Cambridge University Press, Cambridge, England.

Bridal, S., Fornes, P., Bruneval, P., Berger, G., "Correlation of Ultrasonic Attenuation (30 to 50 MHz) and Constituents of Atherosclerotic Plaque", Ultrasound in Medicine and Biology, 1997, pp. 691-703, vol. 23, No. 5, Elsevier, New York, U.S.A.

Bridal, S., Beyssen, B., Fornes, P., Julia, P., Berger, G., "Development of Noninvasive Parametric Imaging of Atherosclerotic Plaque", IEEE Ultrasonics Symposium, 1998, pp. 1595-1598, Institute of Electrical and Electronics Engineers, Piscataway, U.S.A.

Bridal, S., Toussaint, J., Raynaud, J., Fornes, P., Leroy-Willig, A., Berger, G., "US Backscatter and Attenuation 30 to 50 MHz and MR T2 at 3 Tesla for Differentiation of Atherosclerotic Artery Constituents In Vitro", IEEE Transactions on Ultrasonics, Ferroelectrics, and Frequency Control, 1998, pp. 1517-1525, vol. 45, No. 6, Institute of Electrical and Electronics Engineers, New York, U.S.A.

Cherin, E., Saied, A., Laugier, P., Netter, P., Berger, G., "Evaluation of Acoustical Parameter Sensitivity to Age-Related and Osteoarthritic Changes in Articular Cartilage Using 50-MHz Ultrasound", Ultrasound in Medicine and Biology, 1998, pp. 341-354, vol. 24, No. 3, Elsevier, New York, U.S.A.

Cincotti, G., Loi, G., Pappalardo, M., "Frequency Decomposition and Compounding of Ultrasound Medical Images with Wavelet Packets", IEEE Transactions on Medical Imaging, 2001, pp. 764-771, vol. 20, No. 8, Institute of Electrical and Electronics Engineers, New York, U.S.A.

Daubechies, I., "Wavelet Transforms and Orthonormal Wavelet Bases", Proceedings of Symposia in Applied Mathematics, 1993, pp. 1-33, vol. 47, American Mathematic Society, Providence, U.S.A.

De Kroon, M., Van Der Wal, L., Gussenhoven, W., Rusterborgh, H., Bom, N., "Backscatter Directivity and Integrated Backscatter Power of Arterial Tissue", International Journal of Cardiac Imaging, 1991, pp. 265-275, vol. 6, No. 3-4, Nijhoff, Boston, U.S.A.

Georgiou, G., Cohen, F., "Tissue Characterizaton Using the Continuous Wavelet Transform Part I: Decomposition Method", IEEE Transactions on Ultrasonics, Ferroelectrics, and Frequency Control, 2001, pp. 355-363, vol. 48, No. 2, Institute of Electrical and Electronics Engineers, New York, U.S.A.

Georgiou, G., Cohen, F., Piccoli, C., Forsberg, F., Goldberg, B. "Tissue Characterization Using the Continuous Wavelet Transform Part II: Application on Breast RF Data", IEEE Transactions on Ultrasonics, Ferroelectrics, and Frequency Control, 2001, pp. 364-373, vol. 48, No. 2, Institute of Electrical and Electronics Engineers, New York, U.S.A.

Gussenhoven, E., Essed, C., Lancee, C., Mastik, F., Frietman, P., Van Egmond, F., Reiber, J., Bosch, H., Van Urk, H. Roelandt, J., Bom, N., "Arterial Wall Characteristics Determined by Intravascular Ultrasound Imaging: An In Vitro Study", Journal of the American College of Cardiology, 1989, pp. 947-952, vol. 14, No. 4, Elsevier Biomedical, New York, U.S.A.

Gussenhoven, E., Frietman, P. The, S., Van Suylen, R., Van Egmond, F., Lancee, C., Van Urk, H., Roelandt, J., Stunen, T., Bom, N., "Assessment of Medial Thinning in Atherosclerosis by Intravascular Ultrasound", The American Journal of Cardiology, 1991, pp. 1625-1632, vol. 68, No. 17, Cahners Publishing Company, Newton,U.S.A.

Jeremias, A., Kolz, M., Ikonen, T., Gummert, J., Oshima, A., Hayase, M., Honda, Y., Komiyama, N., Berry, G., Morris, R., Yock, P., Fitzgerald, P., "Feasibility of In Vitro Intravascular Ultrasound Tissue Characterization in the Detection of Early Vascular Transplant Rejection", Circulation, 1999, pp. 2127-2130, vol. 100, No. 21, American Heart Association, Dallas, U.S.A.

Kawasaki, M., Takatsu, H., Noda, T., Ito, Y., Kunishima, A., Arai, M., Nishigaki, K., Takemura, G., Morita, N., Minatoguchi, S., Fujiwara, H., "Noninvasive Quantitative Tissue Characterization and Two-Dimensional Color-Coded Map of Human Atherosclerotic Lesions Using Ultrasound Integrated Backscatter-Comparison Between Histology and Integrated Backscatter Images", Journal of the American College of Cardiology, 2001, pp. 486-492, vol. 38, No. 2, Elsevier, New York, U.S.A.

Kawasaki, M., Takatsu, H., Noda, T., Sano, K., Ito, Y., Hayakawa, K., Tsuchiya, K., Arai, M., Nishigaki, K., Takemura, G., Minatoguchi, S., Fujiwara, T., Fujiwara, H., "In Vivo Quantitative Tissue Characterization of Human Coronary Arterial Plaques by Use of Integrated Backscatter Intravascular Ultrasound and Comparison with Angioscopic Findings", Circulation, 2002, pp. 2487-2492, vol. 105, No. 21, American Heart Association, Dallas, U.S.A.

Lizzi, F., Greenbaum, M., Feleppa, E., Elbaum, M., Coleman, D., "Theoretical Framework for Spectrum Analysis in Ultrasonic Tissue Characterization", Journal of the Acoustical Society of America, 1983, pp. 1366-1373, vol. 74, No. 4, American Institute of Physics for the Acoustical Society of America, New York, U.S.A.

Lizzi, F., Astor, M., Feleppa, E., Shao, M., Kalisz, A., "Statistical Framework for Ultrasonic Spectral Parameter Imaging", Ultrasound in Medicine and Biology, 1997, pp. 1371-1382, vol. 23, No. 9, Elsevier, New York, U.S.A.

Lockwood, G., Ryan, L., Hunt, J., Foster, F., "Measurement of the Ultrasonic Properties of Vascular Tissues and Blood from 35-65 MHz", Ultrasound in Medicine and Biology, 1991, pp. 653-666, vol. 17, No. 7, Elsevier, New York, U.S.A.

Marple, S., *Digital Spectral Analysis with Applications*, 1987, pp. 136-144, 154-158, 198-202, 457-458, Prentice-Hall, Inc., Englewood Cliffs, U.S.A.

Moore, M., Spencer, T., Salter, D., Kearney, P., Shaw, T., Starkey, I., Fitzgerald, P., Erbel, R., Lange, A., McDicken, N., Sutherland, G., Fox, K., "Characterisation of Coronary Atherosclerotic Morphology by Spectral Analysis of Radiofrequency Signal: In Vitro Intravascular Ultrasound Study with Histological and Radiological Validation", Heart, 1998, pp. 459-467, vol. 79, No. 5, BMJ Publishing Group, London, England.

Nair, A., Comparison of the Ability of Spectral Algorithms to Predict Atherosclerotic Plaque Composition with Radio Frequency Intravascular Ultrasound Data, Masters Thesis, cataloged on Case Western Reserve University library system Apr. 9, 2001, pp. 1-127, Case Western Reserve University, Cleveland, U.S.A.

Qian, S., Chen, D., "Joint Time-Frequency Analysis", IEEE Signal Processing Magazine, 1999, pp. 52-67, vol. 16, Institute of Electrical and Electronics Engineers, New York, U.S.A.

Rasheed, Q., Nair, R., Sheehan, H., Hodgson, J., "Correlation of Intracoronary Ultrasound Plaque Characteristics in Atherosclerotic Coronoray Artery Disease Patients with Clinical Variables", The American Journal of Cardiology, 1994, pp. 753-758, vol. 73, No. 11, Cahners Publishing Company, Newton U.S.A.

Rohr, K., Stiehl, H., Sprengel, R., Buzug, T., Weese, J., Kuhn, M., "Landmark-Based Elastic Registration Using Approximating Thin-Plate Splines", IEEE Transactions on Medical Imaging, 2001, pp. 526-534, vol. 20, No. 6, Institute of Electrical and Electronics Engineers, New York, U.S.A.

Santosh, K., Tobocman, W., Haacke, E., Izen, S., "In Vivo Biomicroscopy with Ultrasound", Ultrasonics, 1987, pp. 274-282, vol. 25, No. 5, Butterworth & Co., Guildford, England.

Santosh, K., Tobocman, W., Haacke, E., Boada, F., "In Vivo Biomicroscopy with Ultrasound 2", Ultrasonics 1990, pp. 40-49, vol. 28, No. 1, Butterworth & Co., Guildford, England.

Spencer, T., Ramo, M., Salter, D., Sutherland, G., Fox, K., McDicken, W., "Characterisation of Atherosclerotic Plaque by Spectral Analysis of 30 MHz Intravascular Ultrasound Radio Frequency Data", IEEE Ultrasonics Symposium Proceedings, 1996, pp. 1073-1076, vol. 2, Institute of Electrical and Electronics Engineers, New York, U.S.A.

Spencer, T., Ramo, M., Salter, D., Anderson, T., Kearney, P., Sutherland, G., Fox, K., McDicken, W., "Characterisation of Atherosclerotic Plaque by Spectral Analysis of Intravascular Ultrasound: An In Vitro Methodology", Ultrasound in Medicine and Biology, 1997, pp. 191-203, vol. 23, No. 2, Elsevier, New York, U.S.A.

Takiuchi, S., Rakugi, H., Honda, K., Masuyama, T., Hirata, N., Ito, H., Sugimoto, K., Yanagitani, Y., Moriguchi, K., Okamura, A., Higaki, J., Ogihara, T., "Quantitative Ultrasonic Tissue Characterization Can Identify High-Risk Atherosclerotic Alteration in Human Carotid Arteries", Circulation, 2000, pp. 766-770, vol. 102, No. 7, American Heart Association, Dallas, U.S.A.

Tobocman, W., Santosh, K., Carter, J., Haacke, E., "Tissue Characterization of Arteries with 4 MHz Ultrasound", Ultrasonics, 1995, pp. 331-339, vol. 33, No. 4, Elsevier, New York, U.S.A.

Torrence, C., Compo, G., "A Practical Guide to Wavelet Analysis", Bulletin of the American Meteorological Society, 1998, pp. 61-78, vol. 79, No. 1, American Meteorological Society, Boston, U.S.A.

Toussaint, J., Bridal, S., Raynaud, J., Fornes, P., Lebon, V., Leroy-Willig, A., Berger, G., "Magnetic Resonance and Ultrasound Imaging Parameters of Human Aortic and Iliac Atherosclerotic Arteries", 11$^{th}$ International Symposium on Atherosclerosis, 1997, p. 271, Elsevier, New York, U.S.A.

Vince, D., Dixon, K., Cothren, R., Cornhill, J., "Comparison of Texture Analysis Methods for the Characterization of Coronary Plaques in Intravascular Ultrasound Images", Computerized Medical Imaging and Graphics, 2000, pp. 221-229, vol. 24, No. 4, Pergamon Press, New York, U.S.A.

Watson, R., McClean, C., Moore, M., Spencer, T., Salter, D., Anderson, T., Fox, K., McDicken, W., "Classification of Arterial Plaque by Spectral Analysis of In Vitro Radio Frequency Intravascular Ultrasound Data", Ultrasound in Medicine and Biology, 2000, pp. 73-80, vol. 26, No. 1, Elsevier, New York, U.S.A.

Wear, K., Wagner, R., Garra, B., "High Resolution Ultrasonic Backscatter Coefficient Estimation Based on Autoregressive Spectral Estimation Using Burg's Algorithm", IEEE Transactions of Medical Imaging, 1994, pp. 500-507, vol. 13, No. 3, Institute of Electrical and Electronics Engineers, New York, U.S.A.

Wear, K., Wagner, R., Garra, B., "A Comparison of Autoregressve Spectral Estimation Algorithms and Order Determination Methods in Ultrasonic Tissue Characterization", IEEE Transactions on Ultrasonics, Ferroelectrics, and Frequency Control, 1995, pp. 709-716, vol. 42, No. 4, Institute of Electrical and Electronics Engineers, New York, U.S.A.

Weiss, L., Sibul, L., "Weighted Time-Frequency and Time-Scale Transforms for Non-Stationary Signal Detection", Proceedings of SPIE—The International Society for Optical Engineering, 1997, pp. 368-377, vol. 3169, Society of Photo-Optical Instrumentation Engineers, Bellingham, U.S.A.

Wilson, L., Neale, M., Talhami, H., Appleberg, M., "Preliminary Results from Attenuation-Slope Mapping of Plaque Using Intravascular Ultrasound", Ultrasound in Medicine and Biology, 1994, pp. 529-542, vol. 20, No. 6, Elsevier, New York, U.S.A.

Yoshida, K., Yoshikawa, J., Akasaka, T., Hozumi, T., Yamaura, Y., Shakudo, M., Takagi, T., Maeda, K., Okumachi, F., Shiratori, K., Koizumi, K., Minagoe, S., "Intravascular Ultrasound Imaging—In Vitro and In Vivo Validation", Japanese Circulation Journal, 1992, pp. 572-577, vol. 56, No. 6, Japanese Circulation Society, Kyoto, Japan.

Zhang, X., Dejong, S., McKay, C., Collins, S., Sonka, M., "Automated Characterization of Plaque Composition from Intravascular Ultrasound Images", Computers in Cardiology, 1996, pp. 649-652, vol. 23, IEEE Computer Society, Long Beach, U.S.A.

Zhang, X., McKay, C., , Sonka, M., "Tissue Characterization in Intravascular Ultrasound Images", IEEE Transactions on Medical Imaging, 1998, pp. 889-899, vol. 17, No. 6, Institute of Electrical and Electronics Engineers, New York, U.S.A.

Rijsterborgh, H., Mastik, F., Lancee, C., Verdouw, P., Roelandt, J., Bom, N., "Ultrasound Myocardial Integrated Backscatter Signal Processing: Frequency Domain Versus Time Domain", Ultrasound in Medicine and Biology, 1993, pp. 211-219, vol. 19, No. 3, Elsevier, New York, U.S.A.

Schwartz, S., Cao, Q., Vannan, M., Pandian, N., "Automatic Backscatter Analysis of Regional Left Ventricular Systolic Function Using Color Kinesis", American Journal Of Cardiology, 1996, vol. 77, No. 15, pp. 1345-1350, Cahners Publishing Co., Newton, U.S.A.

Silveira, Jr., L., Sathaiah, S., Zangaro, R., Pacheco, M., Chavantes, M., Pasqualucci, C., "Correlation Between Near-Infrared Raman Spectroscopy and the Histopathological Analysis of Atherosclerosis in Human Coronary Arteries", Lasers in Surgery and Medicine, 2002, pp. 290-297, vol. 30, No. 4, Wiley-Liss, New York, U.S.A.

Talhami, H., Wilson, L., Neale, M., "Spectral Tissue Strain: A New Technique for Imaging Tissue Strain Using Intravascular Ultrasound", Ultrasound in Medicine and Biology, 1994, pp. 759-772, vol. 20, No. 8, Elsevier, New York, U.S.A.

* cited by examiner

*Primary Examiner*—Francis J. Jaworski
(74) *Attorney, Agent, or Firm*—O'Melveny & Myers LLP

(57) ABSTRACT

A system and method is provided for using backscattered data and known parameters to characterize vascular tissue. Specifically, in one embodiment of the present invention, an ultrasonic device is used to acquire RF backscattered data (i.e., IVUS data) from a blood vessel. The IVUS data is then transmitted to a computing device and used to create an IVUS image. The blood vessel is then cross-sectioned and used to identify its tissue type and to create a corresponding image (i.e., histology image). A region of interest (ROI), preferably corresponding to the identified tissue type, is then identified on the histology image. The computing device, or more particularly, a characterization application operating thereon, is then adapted to identify a corresponding region on the IVUS image. To accurately match the ROI, however, it may be necessary to warp or morph the histology image to substantially fit the contour of the IVUS image. After the corresponding region is identified, the IVUS data that corresponds to this region is identified. Signal processing is then performed and at least one parameter is identified. The identified parameter and the tissue type (e.g., characterization data) is stored in a database. In another embodiment of the present invention, the characterization application is adapted to receive IVUS data, determine parameters related thereto (either directly or indirectly), and use the parameters stored in the database to identify a tissue type or a characterization thereof.

22 Claims, 3 Drawing Sheets

SYSTEM AND METHOD OF CHARACTERIZING VASCULAR TISSUE

CROSS-REFERENCE TO RELATED APPLICATIONS

This application claims the benefit pursuant to 35 U.S.C. § 119(e) of U.S. Provisional Patent Application Nos. 60/406,183, filed Aug. 26, 2002, 60/406,254, filed Aug. 26, 2002, 60/406,148, filed Aug. 26, 2002, 60/406,184, filed Aug. 26, 2002, 60/406,185, filed Aug. 26, 2002, and 60/406,234, filed Aug. 26, 2002, all of which are incorporated herein, in their entirety, by reference.

BACKGROUND OF THE INVENTION

1. Field of the Invention

The present invention relates to vascular tissue, or more particularly, to a system and method of using backscattered data and known parameters to characterize vascular tissue.

2. Description of Related Art

The present invention relates to the intra-vascular ultrasound (IVUS) analysis arts. It finds particular application to a system and method for quantitative component identification within a vascular object including characterization of tissue. It should be appreciated that while the present invention is described in terms of an ultrasonic device, or more particularly the use of IVUS data (or a transformation thereof) to characterize a vascular object, the present invention is not so limited. Thus, for example, using backscattered data (or a transformation thereof) to characterize any tissue type or composition is within the spirit and scope of the present invention.

Ultrasonic imaging of portions of a patient's body provides a useful tool in various areas of medical practice for determining the best type and course of treatment. Imaging of the coronary vessels of a patient by ultrasonic techniques can provide physicians with valuable information. For example, the image data may show the extent of a stenosis in a patient, reveal progression of disease, help determine whether procedures such as angioplasty or atherectomy are indicated or whether more invasive procedures may be warranted.

In a typical ultrasound imaging system, an ultrasonic transducer is attached to the end of a catheter that is carefully maneuvered through a patient's body to a point of interest such as within a blood vessel. The transducer may be a single-element crystal or probe that is mechanically scanned or rotated back and forth to cover a sector over a selected angular range. Acoustic signals are then transmitted and echoes (or backscatter) from these acoustic signals are received. The backscatter data can be used to identify the type or density of a scanned tissue. As the probe is swept through the sector, many acoustic lines are processed building up a sector-shaped image of the patient. After the data is collected, an image of the blood vessel (i.e., an IVUS image) is reconstructed using well-known techniques. This image is then visually analyzed by a cardiologist to assess the vessel components and plaque content.

Typically, the ultrasonic image data is transferred to a VHS videotape, digitized and then analyzed. This process, however, loses image resolution since the videotape typically has a lower resolution than the originally collected backscatter data. Losing image resolution may result in an inaccurate evaluation of a vessel and its plaque content. Furthermore, certain image characteristics like brightness and contrast will be different for different patients or could vary for the same patient if the cardiologist varies the settings on the IVUS console. The images that are recorded on the videotapes are the same images viewed on the IVUS console screen and, thus, subject to the settings on the console. Since plaque (or tissue type) is identified by its appearance on the screen, errors may occur in the analysis if the screen settings have been modified. Another drawback is that certain information (e.g., tissue composition, etc.) cannot readily be discerned from an IVUS image (at least not to any degree of certainty). Thus, it would be advantageous to have a system and method of characterizing and/or imaging a vascular object that overcomes at least one of these drawbacks.

SUMMARY OF THE INVENTION

The present invention provides a system and method of using backscattered data and known parameters to characterize vascular tissue. Embodiments of the present invention operate in accordance with an ultrasonic device and a computing device comprising a characterization application and a database. Specifically, the ultrasonic device (e.g., intra-vascular ultrasound (IVUS) console and IVUS catheter) is used to acquire RF backscattered data (i.e., IVUS data) from a blood vessel. For example, a transducer may be attached to the end of a catheter and carefully maneuvered through a patient's body to a point of interest. The transducer is then pulsed to acquire echoes or backscattered signals (i.e., IVUS data) reflected from the tissue of the vascular object. The IVUS data is then transmitted to the computing device and used (either by the computing device or the IVUS console) to create an IVUS image.

In a first embodiment of the present invention, the characterization application is adapted to receive and store characterization data (e.g., tissue type data, etc.). Specifically, after the vascular object has been interrogated, the vascular object is cross-sectioned for histology. The cross-section is then prepared with a fixing and staining process that is well known in the art. The staining process allows a clinician to identify a tissue type(s). The identified tissue type (e.g., characterization data) is then provided to the characterization application and stored in the database.

In another embodiment of the present invention, the characterization application is further adapted to create a histology image and identify at least one corresponding region on the IVUS image. In this embodiment, digitized data corresponding to the cross-sectioned vascular object is provided to the characterization application. The digitized data is then used to create a histology image. A region of interest (ROI) on the histology image is then identified by the operator. Preferably, the ROI corresponds to the characterization data, as previously provided. The characterization application is then adapted to identify a corresponding region on the IVUS image. To accurately match the ROI, however, it may be necessary to warp or morph the histology image to substantially fit the contour of the IVUS image. This warping removes histological preparation artifacts caused by cutting the tissue. Accordingly, in one embodiment of the present invention, the characterization application is further adapted to morph the histology image by (i) identifying (or receiving identifying data from an operator on) at least one landmark common to both the histology image and the IVUS image, (ii) use a first algorithm (e.g., a morphometric algorithm) to substantially align the corresponding landmarks, and (iii) use a second algorithm (e.g., a thin plate spline (TPS) deformation technique) to substantially align the non-landmark portions of the object.

In another embodiment of the present invention, the characterization application is further adapted to determine and store parameters associated with the ROI portion of the IVUS image. In this embodiment, the characterization application is adapted to identify the IVUS data that corresponds to the ROI on the IVUS image. After the IVUS data has been identified, and in accordance with one embodiment of the present invention, the characterization application is adapted to identify at least one parameter of the IVUS data. In another embodiment of the present invention, the characterization application is adapted to identify at least one parameter after frequency analysis has been performed (e.g., using fast Fourier transform, the Welch periodogram, autoregressive power spectrum (AR) analysis). The identified parameter is then stored in the database, where it is linked to the characterization data. This data (i.e., stored parameters and characterization data) can then be used to identify or characterize vascular tissue.

In a second embodiment of the present invention, the characterization application is adapted to receive IVUS data, determine parameters related thereto, and use the parameters stored in the database (i.e., histology data) to identify tissue type(s) or characterization(s) thereof. In this embodiment, the characterization application is adapted to receive IVUS data from the IVUS console and identify at least one parameter associated therewith (either directly or indirectly). In other words, the parameters may be identified directly from the IVUS data or from a transformation thereof (e.g., after frequency analysis). The identified parameters are then compared to the parameters stored in the database (i.e., histology data). If a match (either exactly or substantially) is found, the related region is correlated to the tissue type (or characterization) stored in the database. In one embodiment of the present invention, the characterization application is further adapted to display a reconstructed image of the interrogated vascular object, where different tissue types are identified using different colors (e.g., discrete colors, grayscales, etc.).

A more complete understanding of the system and method of using backscattered data and known parameters to characterize vascular tissue will be afforded to those skilled in the art, as well as a realization of additional advantages and objects thereof, by a consideration of the following detailed description of preferred embodiments. Reference will be made to the appended sheets of drawings which will first be described briefly.

BRIEF DESCRIPTION OF THE DRAWINGS

FIG. 3 illustrates a cross-section of an exemplary vascular object in-vivo and in-vitro.

FIG. 4 illustrates an alternate embodiment of the computing device depicted in FIG. 1.

DETAILED DESCRIPTION OF THE PREFERRED EMBODIMENT

Preferred embodiments of the present invention operate in accordance with an ultrasonic device and a computing device comprising a characterization application and a database. In the detailed description that follows, like element numerals are used to describe like elements illustrated in one or more figures.

Figure 1:
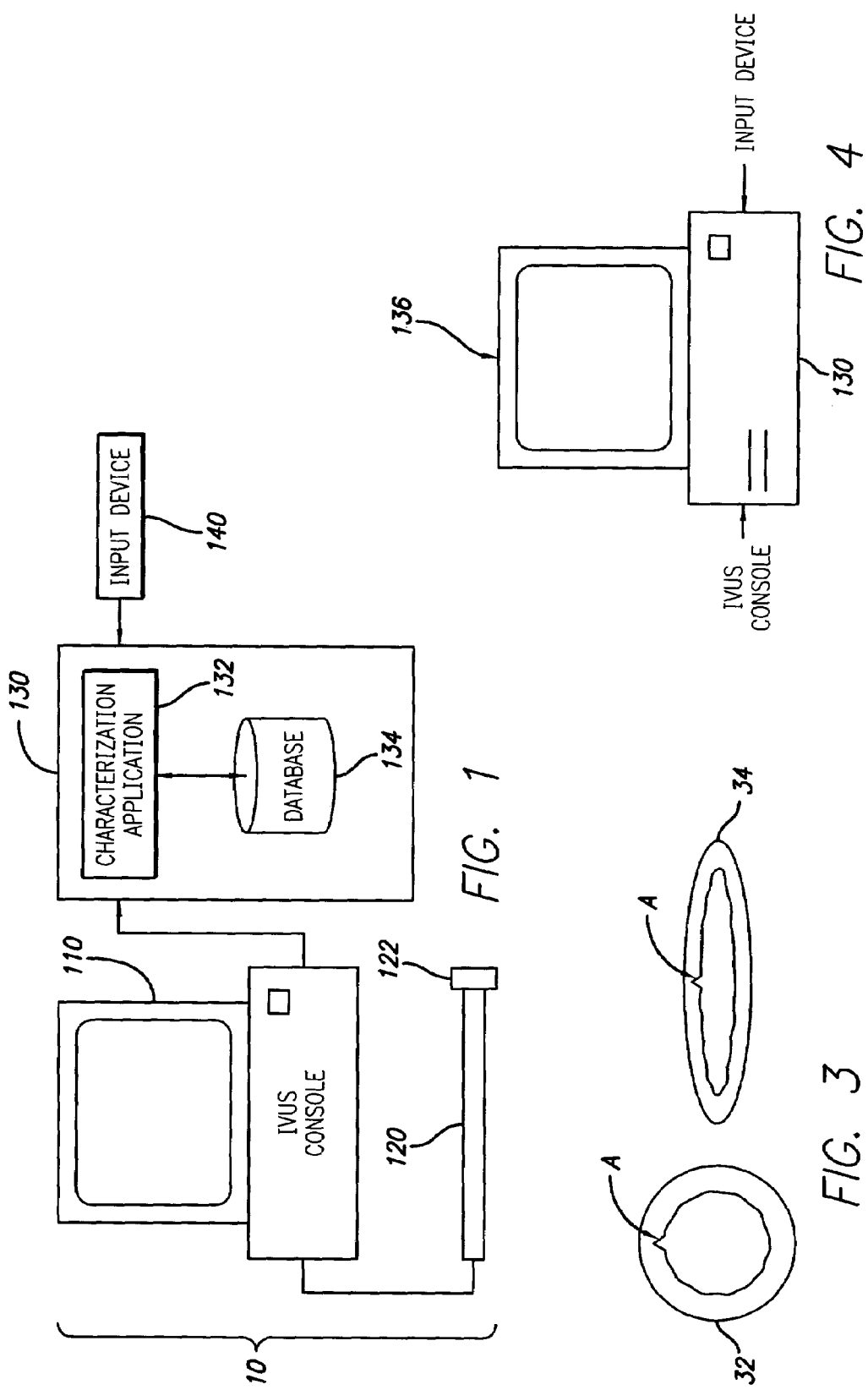
FIG. 1 illustrates a tissue-characterization system in accordance with one embodiment of the present invention, including an IVUS console, an IVUS catheter, a computing device and an input device.
Figure 2:
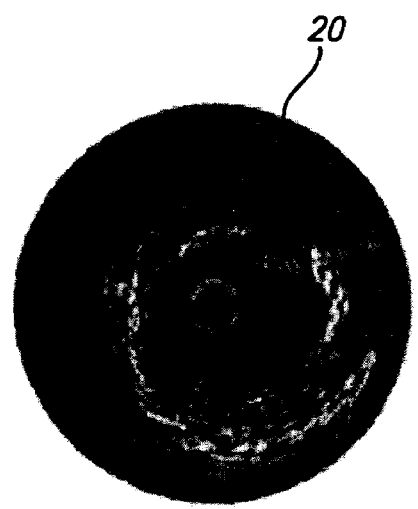
FIG. 2 illustrates an exemplary IVUS image.

FIG. 1 illustrates a tissue-characterization system 10 operating in accordance with a first embodiment of the present invention. In this embodiment, an intra-vascular ultrasound (IVUS) console 110 is electrically connected to an IVUS catheter 120 and used to acquire RF backscattered data (i.e., IVUS data) from a blood vessel. Specifically, a transducer 122 is attached to the end of the catheter 120 and is carefully maneuvered through a patient's body to a point of interest. The transducer is then pulsed to acquire echoes or backscattered signals reflected from the tissue of the vascular object. Because different types and densities of tissue absorb and reflect the ultrasound pulse differently, the reflected data (i.e., IVUS data) can be used to image the vascular object. In other words, the IVUS data can be used (e.g., by the IVUS console 110) to create an IVUS image. An exemplary IVUS image 20 is provided in FIG. 2, where the light and dark regions indicate different tissue types and/or densities. It should be appreciated that the IVUS console 110 depicted herein is not limited to any particular type of IVUS console, and includes all ultrasonic devices known to those skilled in the art (e.g., a C-VIS Clearview Imaging System, etc.). It should further be appreciated that the IVUS catheter 120 depicted herein is not limited to any particular type of catheter, and includes all ultrasonic catheters known to those skilled in the art. Thus, for example, a catheter having a single transducer (e.g., adapted for rotation) or an array of transducers (e.g., circumferentially positioned around the catheter) is within the spirit and scope of the present invention.

Referring back to FIG. 1, the tissue-characterization system 10 further includes a computing device 130 comprising a database 134 and a characterization application 132 electrically connected to the database 134 and adapted to receive IVUS data from the IVUS console 110. It should be appreciated that the database 134 depicted herein includes, but is not limited to, RAM, cache memory, flash memory, magnetic disks, optical disks, removable disks, SCSI disks, IDE hard drives, tape drives and all other types of data storage devices (and combinations thereof, such as RAID devices) generally known to those skilled in the art. It should further be appreciated that the characterization application 132, as depicted and discussed herein, may exist as a single application or as multiple applications, locally and/or remotely stored. It should also be appreciated that the number and location of the components depicted in FIG. 1 are not intended to limit the present invention, and are merely provided to illustrate the environment in which the present invention may operate. Thus, for example, a computing device having a plurality of databases and/or a remotely located characterization application (either in part or in whole) is within the spirit and scope of the present invention.

In one embodiment of the present invention, the characterization application 132 is adapted to receive and store characterization data (e.g., tissue type, etc.). Specifically, after a vascular object has been interrogated (e.g., IVUS data has been collected), a histology correlation is prepared. In other words, the vascular object is dissected or cross-sectioned for histology. In one embodiment of the present invention, the cross-section is previously marked, for example with a suture, so that the histology can be corresponded to a portion of the IVUS image. The cross-section is then prepared with a fixing and staining process that is well known in the art. The staining process allows a clinician to identify a tissue type(s), or a chemical(s) found within (e.g., a chemical corresponding to a particular tissue type, etc.). It should be appreciated that the particular method used to identify or characterize the cross-sectional object is not a limitation of the present invention. Thus, all identification/characterization methods generally known to those skilled in the art are within the spirit and scope of the present invention.

The identified tissue type or characterization (i.e., characterization data) is then provided to the characterization application 132. In one embodiment, as shown in FIG. 1, the characterization data is provided via an input device 140 electrically connected to the computing device 130. The characterization data is then stored in the database 134. It should be appreciated that the input device depicted herein includes, but is not limited to, a keyboard, a mouse, a scanner and all other data-gathering and/or data-entry devices generally known to those skilled in the art. It should further be appreciated that the term tissue type or characterization, as these terms are used herein, include, but are not limited to, fibrous tissues, fibro-lipidic tissues, calcified necrotic tissues, calcific tissues, collagen compositions, cholesterol, thrombus, compositional structures (e.g., the lumen, the vessel wall, the medial-adventitial boundary, etc.) and all other identifiable characteristics generally known to those skilled in the art.

In one embodiment of the present invention, the characterization application is adapted to create a histology image and to identify at least one corresponding region on an IVUS image. Specifically, digitized data is provided to the characterization application (e.g., via the input device 140), where the digitized data corresponds to the cross-sectioned vascular object. The digitized data is then used to create a histology image (i.e., a digital image or outline that substantially corresponds to the vascular object). A region of interest (ROI) on the histology image can then be identified by the operator. Preferably, the ROI is characterized by the characterization data, as previously provided, and may be the entire histology image or a portion thereof. The characterization application is then adapted to identify a corresponding region (e.g., x,y coordinates, etc.) on the IVUS image (i.e., the image created using the raw backscattered data, or the IVUS data).

To accurately match the ROI, however, the histology image may need to be warped to substantially fit the contour of the IVUS image. The warping removes histological preparation artifacts caused by cutting and/or fixing the tissue. For example, as shown in FIG. 3, the shape of a in-vivo vascular object 32 is generally round. Once this object is cut, or cross-sectioned for histology (i.e., creating an in-vitro vascular object 34), the object may appear somewhat distorted, or flattened. Furthermore, the tissue may shrink (e.g., about 30%) when it is put through the fixation process. Thus, in order to identify a corresponding ROI on the IVUS image, the histology image may need to be warped or morphed, to return it to its original shape.

Accordingly, in one embodiment of the present invention, the characterization application is adapted to morph the histology image. Specifically, the characterization application is adapted to identify (or receive identifying data from an operator on) at least one landmark common to both the histology image and the IVUS image (see e.g., FIG. 3, landmark A). The characterization application is then adapted to use (i) a first algorithm (e.g., a morphometric algorithm) to substantially align the corresponding landmarks and (ii) a second algorithm (e.g., a thin plate spline (TPS) deformation technique) to substantially align the non-landmark portions of the object. In other words, the second algorithm is used to shape the regions or boundaries between the landmarks. It should be appreciated that the landmarks discussed herein include, but are not limited to, side branch vessels, identifiable plaque or calcium deposits, and all other vascular tissue landmarks generally known to those skilled in the art.

In one embodiment of the present invention, the characterization application is further adapted to determine and store parameters associated with the ROI portion of the IVUS image. Specifically, the characterization application is adapted to identify the IVUS data (i.e., the raw backscatter data) that corresponds to the ROI identified on the IVUS image. In other words, the IVUS data that was originally used to create the ROI on the IVUS image is identified. In one embodiment of the present invention, the characterization application is further adapted to identify at least one parameter of the identified IVUS data. This parameter is then stored in the database, where it is linked to the characterization data. It should be appreciated, however, that each parameter may be associated with more than one tissue type or characterizations. For example, a first parameter may be common to multiple tissue types, thus requiring additional parameters to narrow the field.

In another embodiment of the present invention, signal analysis (i.e., frequency analysis, etc.) is performed on the identified IVUS data before the parameters are identified. In other words, the IVUS data is converted (or transformed) into the frequency domain (e.g., from the time domain) to identify the frequency spectrum of the ROI. This is because the frequency information obtained from the backscattered signal (or parameters associated therewith) can serve as a "signature" for each tissue type or characteristic. In one embodiment of the present invention, the frequency analysis is performed using a fast Fourier transform (FFT). In another embodiment of the present invention, the frequency analysis is performed using the Welch periodogram. In another embodiment of the present invention, the frequency analysis is performed using autoregressive power spectrum (AR) analysis. At least one parameter of the frequency-based signal is then identified and stored in the database, where it is linked to the characterization data.

In another embodiment of the present invention, both backscattered data (e.g., IVUS data) and its frequency spectrum are analyzed to classify the ROI portion of the IVUS image. Specifically, the frequency spectrum (or more particularly at least one parameter identified therefrom) is used to identify tissue type and the backscattered data is used to identify tissue location. This is because the backscatter data is in the time domain, and can thus be used to spatially identify certain frequencies (or parameters related thereto). For example, if a vascular wall comprises multiple tissue layers, corresponding backscattered data can be used to identify the location of these tissues and the related frequency spectrum can be used to identify tissue types. It should be appreciated that, while certain embodiments have been described in terms of frequency transformation, the present invention is not so limited. Thus, alternate transformations (e.g., wavelet transformation, etc.) are within the spirit and scope of the present invention. It should further be appreciated that the term parameter, as that term is used herein, includes, but is not limited to maximum power, minimum power, frequencies at maximum and/or minimum power, y intercepts (estimated or actual), slope, mid-band fit, integrated backscatter and all parameters generally known to (or discernable by) those skilled in the art. It should also be appreciated that the term "histology data," as that term is used herein, includes data stored in the database (e.g., characterization data, parameters, etc.).

Figure 6:
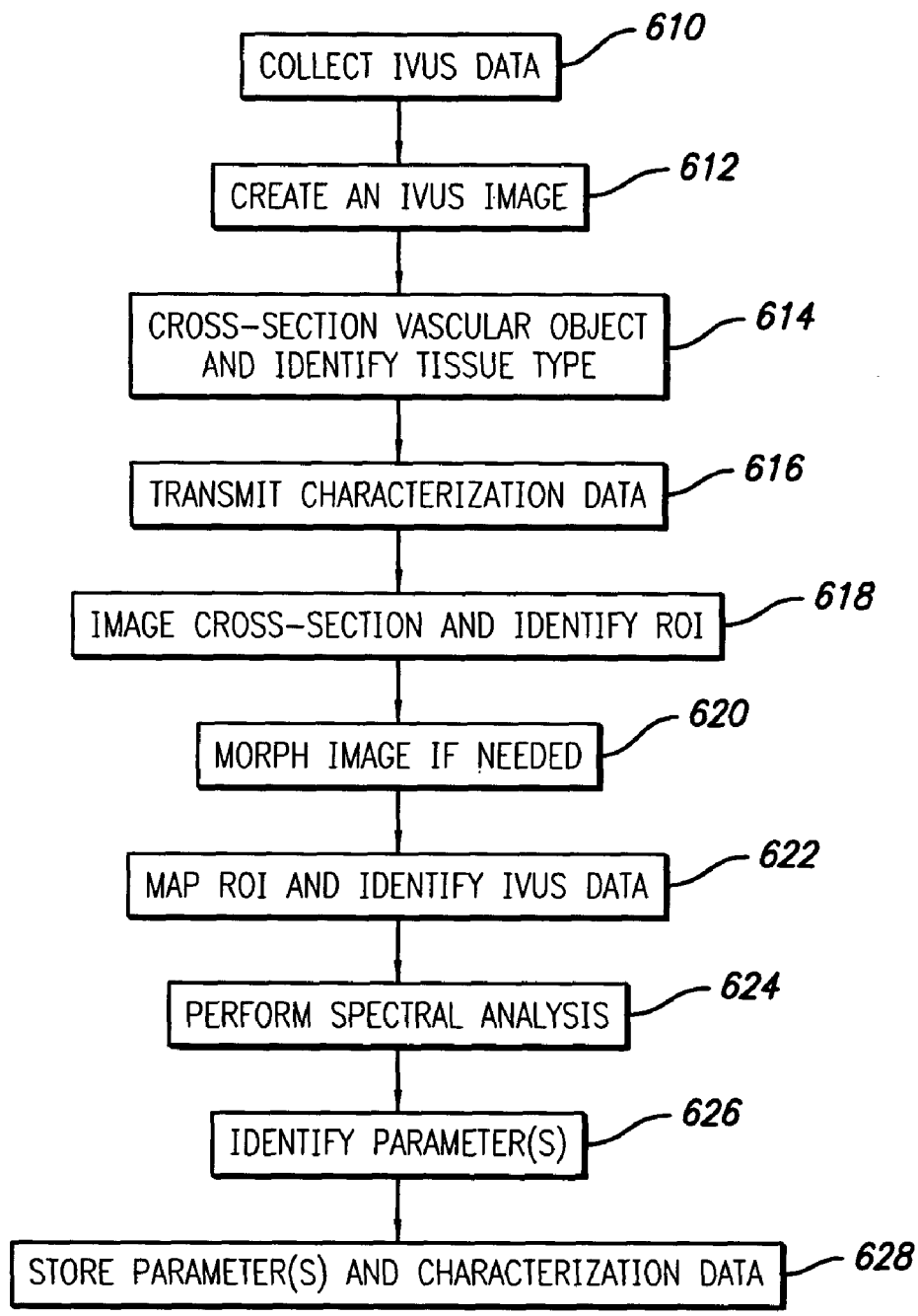
FIG. 6 illustrates a method of characterizing a vascular object in accordance with one embodiment of the present invention.

One method of populating the database is illustrated in FIG. 6. Specifically, at step 610, IVUS data (i.e., RF backscatter data) is collected from a portion of a vascular object. This data is then used to create an IVUS image at step 612. At step 614, the interrogated portion of the vascular object is cross-sectioned and a tissue type (or a characterization thereof) is identified. This information (i.e., characterization data) is then transmitted to a computing device (or the equivalent thereof) at step 616. At step 618, an image of the cross-sectioned vascular object is created and a ROI is identified (e.g., by an operator). This image is then morphed, if needed, to substantially match the cross-section image to the IVUS image at step 620. This may include identifying at least one landmark and applying at least one algorithm (e.g., a morphometric algorithm, a TPS deformation technique, etc.). At step 622, the ROI is mapped to the IVUS image and associated IVUS data is identified. Spectral analysis is then performed on the associated IVUS data at step 624, and at least one parameter is identified at step 626. The at least one parameter and the characterization data is then stored at step 628. In one embodiment of the present invention, the at least one parameter is stored such that it is linked to the characterization data. It should be appreciated that the order in which these steps are presented is not intended to limit the present invention. Thus, for example, creating an IVUS image after the vascular object is cross-sectioned is within the spirit and scope of the present invention.

The above-described process is repeated for each tissue component desired to be identified and repeated for each component as many times as desired in order to obtain a more accurate range of signal properties. With the database populated, a tissue type or characteristic can be automatically and accurately identified if the acquired parameters substantially match parameters stored in the database.

Accordingly, in a second embodiment of the present invention, the characterization application is adapted to receive IVUS data, determine parameters related thereto, and use the parameters stored in the database (i.e., histology data) to identify tissue type(s) or characterization(s) thereof. Specifically, with reference to FIG. 1, the characterization application 132 is adapted to receive IVUS data from the IVUS console 110. The characterization application 132 is then adapted to identify at least one parameter associated (either directly or indirectly) with the IVUS data. It should be appreciated that the IVUS data may either be received in real-time (e.g., while the patient is in the operating room) or after a period of delay (e.g., via CD-ROM, etc.). It should further be appreciated that the identified parameters should be related (generally) to the stored parameters. Thus, for example, an estimated Y intercept parameter should be identified if data related to a signal's estimated Y intercept is stored in the database 134 and linked to at least one tissue type. Moreover, if the stored parameters were acquired after frequency analysis was performed (i.e., are related to a frequency-based signal), then frequency analysis (preferably of the same type) should be performed on the IVUS data before parameters are identified. However, the IVUS data may be used to identify spatial information, as previously discussed.

The identified parameters are then compared to the parameters stored in the database (i.e., histology data). If a match (either exactly or substantially) is found, the related region is correlated to the tissue type (or characterization) stored in the database 134 (e.g., as linked to the matching parameters). It should be appreciated that a match may occur as long as the parameters fall within a range of properties for a particular tissue type found in the database.

Figure 5:
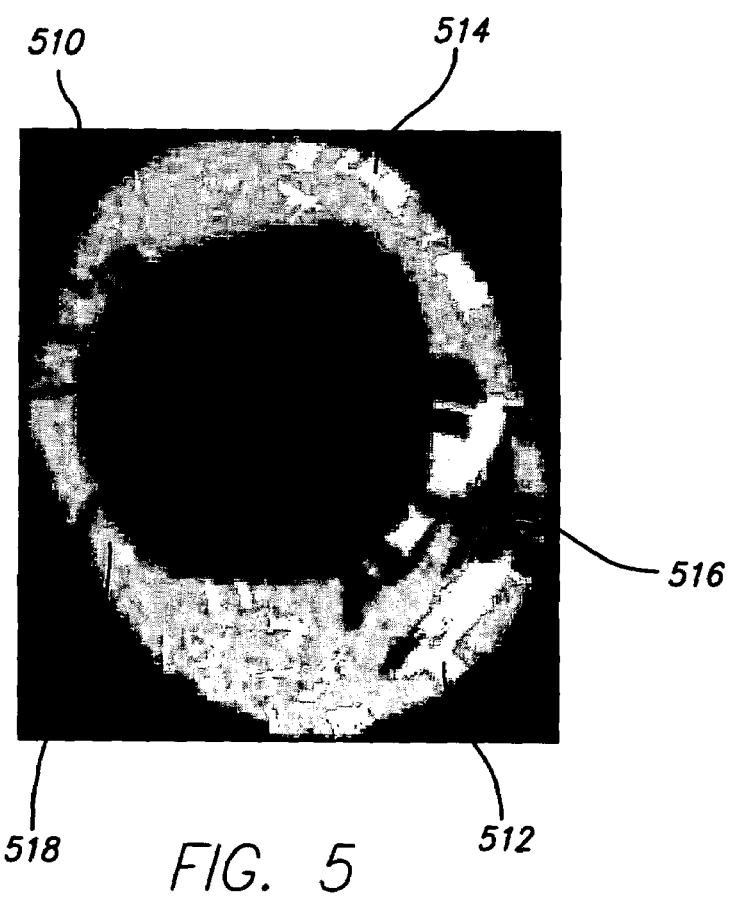
FIG. 5 illustrates an exemplary image of a characterized vascular object.

In one embodiment, after each region is identified, the characterization application is further adapted to display a reconstructed image of the interrogated vascular object on a display. A computing device 130 including such a display 136 is illustrated in FIG. 4. In one embodiment of the present invention, each tissue type (or characterization) is distinguished through the use of gray-scales or discrete colors. For example, FIG. 5 illustrates an exemplary reconstructed vascular object 510, where different tissues (e.g., calcific tissues 512, fibrous tissues 514, calcified necrotic tissues 516 and fibro-lipidic tissues 518) are identified using different shades of gray. Such a system makes different tissue types or characterizations easily identifiable. Additional examples of characterized vascular objects are provided by U.S. Pat. No. 6,200,268, which was issued on Mar. 13, 2001, and is incorporated herein, in its entirety, by reference. It should be appreciated that the reconstructed vascular object may further identify vascular borders. Systems and methods of identifying vascular borders are provided by U.S. Provisional Application Nos., 60/406,184, 60/406,234, and 60/406,185, which were filed Aug. 26, 2002, and by U.S. Pat. No. 6,381,350, which issued Apr. 30, 2002, and are incorporated herein, in their entirety, by reference.

Having thus described embodiments of a system and method of using backscattered data and known parameters to characterize a vascular tissue, it should be apparent to those skilled in the art that certain advantages of the system have been achieved. It should also be appreciated that various modifications, adaptations, and alternative embodiments thereof may be made within the scope and spirit of the present invention. The invention is further defined by the following claims.

What is claimed is:

1. A method of characterizing vascular tissue, comprising:
   collecting RF backscatter data from a portion of a vascular object;
   using at least said RF backscatter data to construct a first image of said portion of said vascular object;
   preparing a histology of said portion of said vascular object;
   using said histology to construct a second image of said portion of said vascular object;
   characterizing at least a portion of said histology;
   identifying a region of interest (ROI) of said second image, said ROI corresponding to said at least a portion of said histology;
   identifying at least one landmark common to said first and second images and using said at least one landmark to identify a region of said first image that substantially corresponds to said ROI of said second image said step of identifying at least one further landmark comprising applying a morphometric algorithm to align the at least one landmark of said second image to substantially match the at least one landmark of said first image, said step of identifying at least one landmark further comprising applying a morphometric algorithm to align the at least one landmark of said second image to substantially match the at least one landmark of said first image;

identifying a portion of said RF backscatter data corresponding to said region of said first image;
identifying at least one parameter of said RF backscatter data; and
storing said at least one parameter and said characterization of said at least a portion of said histology.

2. The method of claim 1, wherein said step of identifying at least one parameter further comprises performing a frequency transformation on said portion of said RF backscatter data before said at least one parameter is identified.

3. The method of claim 2, wherein said step of performing a frequency transformation further comprises using a fast Fourier transform (FFT).

4. The method of claim 2, wherein said step of performing a frequency transformation further comprises using the Welch periodogram.

5. The method of claim 2, wherein said step of performing a frequency transformation further comprises using autoregressive power spectrum (AR) analysis.

6. The method of claim 1, wherein said step of identifying at least one parameter further comprises performing a wavelet transformation on said portion of said RF backscatter data before said at least one parameter is identified.

7. The method of claim 1, wherein said step of identifying at least one landmark further comprises aligning the non-landmark portions of said first and second images based on a thin plate algorithm.

8. The method of claim 1, wherein said step of characterizing at least a portion of said histology further comprises identifying a tissue type, said tissue type being selected from a group consisting of fibrous tissues, fibro-lipidic tissues, calcified necrotic tissues, and calcific tissues.

9. The method of claim 1, wherein said step of identifying at least one parameter further comprises identifying said at least one parameter from a group consisting of maximum power, minimum power, frequency at maximum power, frequency at minimum power, y intercept, slope, mid-band fit, and integrated backscatter.

10. The method of claim 1, further comprising:
collecting a second set of RF backscatter data from a second vascular object;
performing a frequency transformation on at least a portion of said second set of RF backscatter data to produce a third set of data;
identifying at least another parameter from a third set of data; and
using said at least another parameter, said at least one parameter and said characterization of said at least a portion of said histology to characterize at least a portion of said second vascular object.

11. A vascular-tissue-characterization system, comprising:
a computing device comprising:
a database; and
a characterization application electrically connected to said database and adapted to:
receive intra-vascular ultrasound (IVUS) data corresponding to a portion of a vascular object and digitized data corresponding to a histology of said portion of said vascular object;
use at least said IVUS data and said digitized data to construct a first and second image, respectively, of said portion of said vascular object;
receive characterization data corresponding to a region of interest (ROI) of said second image;
use at least one landmark to morph said second image to substantially match said first image and to identify said ROI on said first image;
identify a portion of said IVUS data corresponding to said ROI on said first image;
identify at least one parameter related to said portion of said IVUS data; and
store said at least one parameter and said characterization data in said database, said characterization application being further adapted to use a morphometric algorithm to align the at least one landmark of said second image to substantially match the at least one landmark of said first image said charecterization application being further adapted to use a morphometric algorithm to align the at least one landmark of said second image to substantially match the at least one landmark of said first image.

12. The vascular-tissue-characterization system of claim 11, wherein said characterization application is further adapted to perform a spectral analysis on said IVUS data before said at least one parameter is identified.

13. The vascular-tissue-characterization system of claim 12, wherein said characterization application is further adapted to perform the Welch periodogram.

14. The vascular-tissue-characterization system of claim 12, wherein said characterization application is further adapted to analyze said IVUS data to identify at least one location corresponding to said at least one parameter.

15. The vascular-tissue-characterization system of claim 12, wherein said characterization application is further adapted to perform a fast Fourier transform (FFT).

16. The vascular-tissue-characterization system of claim 15, wherein said characterization application is further adapted to perform autoregressive power spectrum (AR) analysis.

17. The vascular-tissue-charecterization system of claim 11, wherein said at least one parameters is selected from a group consisting of maximum power, minimum power, frequency at maximum power, frequency at minimum power, y intercept, slope, mid-band fit, and integrated backscatter.

18. The vascular-tissue-characterizatiOn system of claim 11, wherein said characterization data comprises a tissue type, said tissue type being selected from a group consisting of fibrous tissues, fibro-lipidic tissues, calcified necrotic tissues, and calcific tissues.

19. The vascular-tissue-characterization system of claim 11, further comprising an input device electrically connected to said computing device, said characterization data being provided by said input device.

20. The vascular-tissue-characterization system of claim 11, further comprising an IVUS console adapted to:
acquire said IVUS data from said vascular object; and
provide said IVUS data to said computing device.

21. The vascular-tissue-characterization system of claim 20, further comprising an IVUS catheter having at least one transducer, said IVUS catheter being electrically connected to said IVUS console and adapted to acquire said IVUS data from said vascular object.

22. The vascular-tissue-characterization system of claim 11, wherein said characterization application is further adapted to align the non-landmark portions of said first and second images based on a thin plate algorithm.

* * * * *

UNITED STATES PATENT AND TRADEMARK OFFICE
CERTIFICATE OF CORRECTION

PATENT NO. : 7,074,188 B2 Page 1 of 1
APPLICATION NO. : 10/647971
DATED : July 11, 2006
INVENTOR(S) : Nair et al.

It is certified that error appears in the above-identified patent and that said Letters Patent is hereby corrected as shown below:

Col. 8, lines 58-62 (Claim 1), "said step of identifying at least one further landmark comprising applying a morphometric algorithm to align the at least one landmark of said second image to substantially match the at least one landmark of said first image" should be deleted.

Col. 10, lines 14-18 (Claim 11), "said charecterization application being further adapted to use a morphometric algorithm to align the at least one landmark of said second image to substantially match the at least one landmark of said first image" should be deleted.

Col. 10, lines 33-34 (Claim 16), "claim 15" should be changed to -- claim 12 --.

Col. 10, line 37 (Claim 17), "vascular-tissue-charecterization" should be changed to -- vascular-tissue-characterization --.

Col. 10, line 43 (Claim 18), "vascular-tissue-characterizatiOn" should be changed to -- vascular-tissue-characterization --.

Signed and Sealed this

Tenth Day of April, 2007

JON W. DUDAS
*Director of the United States Patent and Trademark Office*